(12) United States Patent
Eriksson et al.

(10) Patent No.: US 10,307,692 B2
(45) Date of Patent: Jun. 4, 2019

(54) CHROMATOGRAPHY COLUMN AND METHOD OF CONDUCTING MAINTENANCE ON A CHROMATOGRAPHY COLUMN

(71) Applicant: GE Healthcare Bio-Sciences AB, Uppsala (SE)

(72) Inventors: Stefan Kjell Eriksson, Uppsala (SE); Andreas Bergstrom, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 698 days.

(21) Appl. No.: 14/409,167

(22) PCT Filed: Jun. 18, 2013

(86) PCT No.: PCT/SE2013/050710
§ 371 (c)(1),
(2) Date: Dec. 18, 2014

(87) PCT Pub. No.: WO2013/191627
PCT Pub. Date: Dec. 27, 2013

(65) Prior Publication Data
US 2015/0336027 A1    Nov. 26, 2015

(30) Foreign Application Priority Data
Jun. 21, 2012  (SE) ...................................... 1250667

(51) Int. Cl.
*B01D 15/10* (2006.01)
*B01D 15/22* (2006.01)
(Continued)

(52) U.S. Cl.
CPC ............. *B01D 15/22* (2013.01); *B01D 15/10* (2013.01); *G01N 30/60* (2013.01);
(Continued)

(58) Field of Classification Search
CPC ........ B01D 15/22; B01D 15/10; G01N 30/60; G01N 30/6047; G01N 30/56; G01N 30/6021; G01N 30/6004; G01N 30/6017
See application file for complete search history.

(56) References Cited

U.S. PATENT DOCUMENTS

| 5,167,809 A | 12/1992 | Mann et al. | |
|---|---|---|---|
| 7,452,464 B2 * | 11/2008 | Uselius | B01D 15/22 210/198.2 |

(Continued)

FOREIGN PATENT DOCUMENTS

| EP | 0476998 A2 | 3/1992 |
|---|---|---|
| EP | 2324898 A2 | 5/2011 |

(Continued)

OTHER PUBLICATIONS

International Search Report issued in connection with corresponding WO application PCT/SE2013/ 050710 dated Sep. 23, 2013.
(Continued)

*Primary Examiner* — Katherine Zalasky
*Assistant Examiner* — Benjamin L Lebron
(74) *Attorney, Agent, or Firm* — Wood IP LLC

(57) ABSTRACT

A chromatography column including: a tubular housing; a first end unit removably connected to a first end of the tubular housing; a second end unit removably connected to a second end of the tubular housing; an adaptor assembly movable within said tubular housing; an adaptor rod connected to said adaptor assembly, which adaptor rod is arranged to extend through an opening in the first end unit; a filter removably connected to the adaptor assembly; and a frame connected to said tubular housing for supporting the column on a floor. At least an actuating means is arranged on the frame, so that the column can be lifted and lowered in a substantially vertical direction.

20 Claims, 18 Drawing Sheets

(51) Int. Cl.
*G01N 30/60* (2006.01)
*G01N 30/56* (2006.01)

(52) U.S. Cl.
CPC ..... *G01N 30/6004* (2013.01); *G01N 30/6017* (2013.01); *G01N 30/6047* (2013.01); *G01N 30/56* (2013.01); *G01N 30/6021* (2013.01); *Y10T 29/49828* (2015.01)

(56) References Cited

U.S. PATENT DOCUMENTS

| | | | |
|---|---|---|---|
| 7,708,891 | B2 | 5/2010 | Davis et al. |
| 2005/0011835 | A1 | 1/2005 | Henederson et al. |
| 2008/0308498 | A1 | 12/2008 | Davis et al. |
| 2009/0039008 | A1 | 2/2009 | Davis et al. |
| 2011/0120951 | A1* | 5/2011 | Hampton ............ B01D 15/206 210/657 |

FOREIGN PATENT DOCUMENTS

| | | |
|---|---|---|
| GB | 2476320 A | 6/2011 |
| JP | H04273059 A | 9/1992 |
| JP | 2009-079896 A | 4/2009 |
| WO | 2009093952 A1 | 7/2009 |
| WO | 2011162678 A1 | 12/2011 |
| WO | 2013/191627 A1 | 12/2013 |

OTHER PUBLICATIONS

Office Action received for Japanese Patent Application No. 2015-518371, dated Jan. 24, 2017, 3 pages. (1 page English Communication + 2 pages Official Copy).

International Preliminary Report on Patentability received for PCT Patent Application No. PCT/SE2013/050710, dated Dec. 23, 2014, 6 pages.

* cited by examiner

CHROMATOGRAPHY COLUMN AND METHOD OF CONDUCTING MAINTENANCE ON A CHROMATOGRAPHY COLUMN

CROSS-REFERENCE TO RELATED APPLICATIONS

This is a national stage application under 35 U.S.C. § 371(c) of prior-filed, copending, PCT application serial number PCT/SE2013/050710, filed on Jun. 18, 2013, which claims priority to Swedish patent application serial number 1250667-1, filed on Jun. 21, 2012, the entire contents of which are incorporated by reference herein.

TECHNICAL FIELD OF THE INVENTION

Embodiments of the present invention relate to a chromatography column and a method of conducting maintenance on a chromatography column.

Performing maintenance on chromatography columns, especially columns in industrial-scale chromatography, is necessary for cleaning and replacing bed supports, distributor plates and sliding rings. Heavy lifting equipment such as hoists or cranes to dismantle the columns has an influence on safety and time efficiency when performing maintenance. Embodiments of the invention are concerned with efficient and safer methods for performing maintenance on such columns.

BACKGROUND ART

The chromatography technique is widely used in different forms for separating chemical and biological substances and there are many applications in compound preparation, purification and analysis. Liquid chromatography is of particular importance in the pharmaceutical and biological industries for the preparation, purification and analysis of proteins, peptides and nucleic acids.

A typical liquid chromatography apparatus has an upright housing in which a bed of packing material, which is usually particulate in nature and consists of a porous medium, rests against a permeable retaining layer. A liquid mobile phase enters through an inlet, for example at the end of an adaptor rod which has an elongated extension within the column. The liquid mobile phase thereafter enters a distributor plate which distributes the liquid mobile phase through a porous, perforated filter, mesh, frit or net, which together with the distributor plate is arranged on an adaptor. The liquid mobile phase thereafter moves through the bed of packing material and is finally removed via an outlet, typically through a second filter, mesh, frit or net and a second distributor plate.

Columns used in liquid chromatography typically comprise a tubular body enclosing the porous chromatography medium through which the carrier liquid or mobile phase flows, with separation of substances or analytes taking place between the mobile phase and solid phase of the porous medium. Typically, the porous medium is enclosed in the column as a packed bed, generally formed by consolidating a suspension of discrete particles, known as slurry that is pumped, poured or sucked into the column, usually from a bore or nozzle located at a tubular housing or at one end of the column. The production of a stable, even bed is often critical to the final separation process.

Conventional distribution systems for use in liquid chromatography comprise a distributor plate attached to the net. The distributor plate comprises channels arranged in a pattern to substantially uniform distribute the fluid over the plate. The distributor plate is perforated with holes or openings which lead the fluid from the channels and uniformly into the packed bed.

During the chromatography process the packed bed may be damaged and fines may occur in the column. After several chromatography cycles the fines may clog the net or nets in the column, which may result in higher back pressure and lower process efficiency. Therefore, maintenance of the chromatography columns must be conducted frequently and the nets or filters must be replaced after a number of cycles.

The backing plate or the lowermost, second end unit of the chromatography columns generally acts as a support for the column, being itself supported on legs or some other stand arrangement positioned on the floor which allows clearance for outlet pipe work projecting beneath the column.

When such a column requires maintenance to, or cleaning of, internal components, such as the valves, seals, meshes/screens/filters, distribution systems etc., heavy lifting gear such as a crane or hoist is necessary to lift the upper end/adaptor assembly away from the column tube and the column tube away from the lower end/base assembly as these assemblies can weigh in excess of three tons. The use of heavy overhead lifting equipment to disassemble the column in order to carry out internal maintenance is not desirable. Operator safety is obviously a concern when heavy equipment is lifted overhead and technicians exposed below. Furthermore, alignment structures are required to keep the column and its base/adaptor assemblies axially aligned as they are separated from each other, to avoid damage to the precision components.

The presence of such alignment and lifting structures imposes significant obstructions around the tube and need to be carefully laid out to provide sufficient clearance at some point of the circumference for insertion/removal of the internal components. Furthermore, the requirement to use heavy lifting equipment imposes constraints on housing such columns, sufficient overhead space and support being required to accommodate hoists or cranes. As many chromatography columns are now run in "clean" environments under GMP, to avoid microbiological contamination, where it is extremely difficult to accommodate overhead equipment, the requirement of moving the column to another room for disassembly and maintenance is problematic. This problem is exacerbated by the need to clean and verify the column before returning it for use to the clean environment. The presence of hoists or cranes in GMP facilities used for biopharmaceutical manufacturing is thus highly undesirable for the above mentioned reasons, together with the fact that these machines shed particulate matter, in the form of dirt, during their operation and maintenance.

U.S. Pat. No. 6,736,974 addresses some of the above problems by providing a column which is capable of lifting the adaptor assembly above the column tube and/or raising the column tube above the base assembly by means of an hydraulic system which is integral to the column.

However, the system described in U.S. Pat. No. 6,736,974 has significant disadvantages associated with it by virtue of its design. As can be seen from FIGS. 4 and 5 of U.S. Pat. No. 6,736,974 and described in column 4, lines 63-66 of that document, in order to remove the distributor plate (31) and/or filter/mesh (28/60) from the interior of the column, the operator must work within the centre of the drum (18) to access and remove the fixing nut (30) which secures these component parts. As industrial columns typically have diameters ranging from about 200 mm to 2000 millimeters, this means that the operator must work below a suspended or supported load to unscrew the nut. This clearly poses a significant safety risk to the operator, particularly where the operator's arm or head is exposed below the suspended or supported load.

Furthermore, once the column tube/cylinder or adaptor assembly has been raised from the base assembly or tube, respectively, removal of the heavy bed support and/or distributor from the column can only be accomplished by tilting the bed support or distributor at an angle to negotiate the hydraulic drive pistons or safety rods. This can clearly be seen from, for example, FIGS. 3, 4 and 5 in which the distance between any two safety rods (69) or between any two hydraulic pistons (36) is less than the diameter of the mesh/filter (28/60) or distributor plate (31). The same problem would exist for the base or adaptor bed support (not shown).

Removal of these internal components, which could weigh in excess of 100 kg, requires considerable manhandling by the operator and necessitates their being exposed below the suspended column or adaptor assembly. Once again, this represents a significant safety risk for the operator.

The task of physically removing the heavy bed support or distributor, as described in U.S. Pat. No. 6,736,974, must be carried out by an operator, there being no disclosure of the use of any lifting aid to assist in this task. The configuration of the hydraulic pistons and the safety rods, and the need to tilt the bed support and/or distributor in order to avoid hitting these supporting structures in withdrawing these components from the column, would require the design of a bespoke lifting device.

Document WO 2005/056156 also discloses a column which can be accessed for maintenance without the need for a crane or hoist. The column is designed such that the tube and the base assembly can be separated by means of hydraulic drive cylinders to provide an access space between them to conduct maintenance or service on the base assembly. The piston of the adaptor assembly can be advanced through the column tube to expose it at the open end of the column tube, i.e. in the space between the tube and the base assembly, for maintenance. However, as is evident from this document (for example, FIGS. 19 and 20 and related description on page 23) access to release the fastening screws retaining the bed support or mesh/filter in place is provided by the space between the tube and the base assembly. Removal of the bed support necessitates the operator being exposed to a suspended load while retaining screws are removed. Furthermore, the distance between any two drive cylinders for maintenance access is less than the diameter of the bed support, which requires the operator to manhandle and tilt the bed support when removing or replacing it. Maintenance of the column thus imposes a significant safety risk for the operator.

According to known chromatography columns the nets are welded or heat shrinked on the distributor plate, which distributor plate in turn is removably connected by fastening elements on the adaptor. Time and cost consuming operations are necessary in order to remove the clogged net from the distributor plate. Especially, when the chromatography column is of a large size the removal of the net from the distributor plate by using milling or turning machines is complicated. The replaced net must be welded or heat shrinked on the distributor plate before remounting on the adaptor. The chromatography column may not be used under a substantially period of time during the replacement of the nets. This may lead to production losses in the pharmaceutical and biological industries.

Notwithstanding the existence of such prior art chromatography column filters, there is a need to improve the maintenance methods available for chromatography columns by providing columns which are safer and easier for operators to use. Also, there is a need to reduce cost and time when conducting maintenance on chromatography columns. Also, there is a need to reduce complexity and to reduce needed floor space when conducting maintenance on chromatography columns.

SUMMARY OF THE INVENTION

An objective problem to be solved by the present invention is to reduce cost when conducting maintenance on chromatography columns.

Another objective problem to be solved by the present invention is to reduce time when conducting maintenance on chromatography columns.

Still another objective problem to be solved by the present invention is to increase safety when conducting maintenance on chromatography columns.

Still another objective problem to be solved by the present invention is to reduce complexity when conducting maintenance on chromatography columns.

Still another objective problem to be solved by the present invention is to reduce needed floor space when conducting maintenance on chromatography columns.

These objects above are achieved by a chromatography column according to claim 1 and a method of conducting maintenance on a chromatography column according to claim 6.

The method according to the invention eliminates the need for hoist and surrounding equipment which increases the cost when conducting maintenance on chromatography columns. Also, the method provides for easier and less time consuming maintenance on chromatography columns because a number operation steps can be eliminated in comparison with known maintenance methods. Therefore, the efficiency when conducting maintenance on such column increases. The demand for a large floor space when dismantle the column is also eliminated by the method. The elimination of heavy lifting equipment, such as separate hoists or cranes to dismantle the column, increase safety to equipment and maintenance personnel when conducting maintenance on such columns.

The invention accordingly comprises the method of maintenance, the features of construction, combination of elements, and arrangement of parts that will be exemplified in the description set forth hereinafter and the scope of the invention will be indicated in the claims.

BRIEF DESCRIPTION OF THE DRAWINGS

Further aspects, advantages and features of the invention can be derived from the following detailed description of exemplary embodiments of the invention, with reference to the drawings.

DETAILED DESCRIPTION

Figure 1:
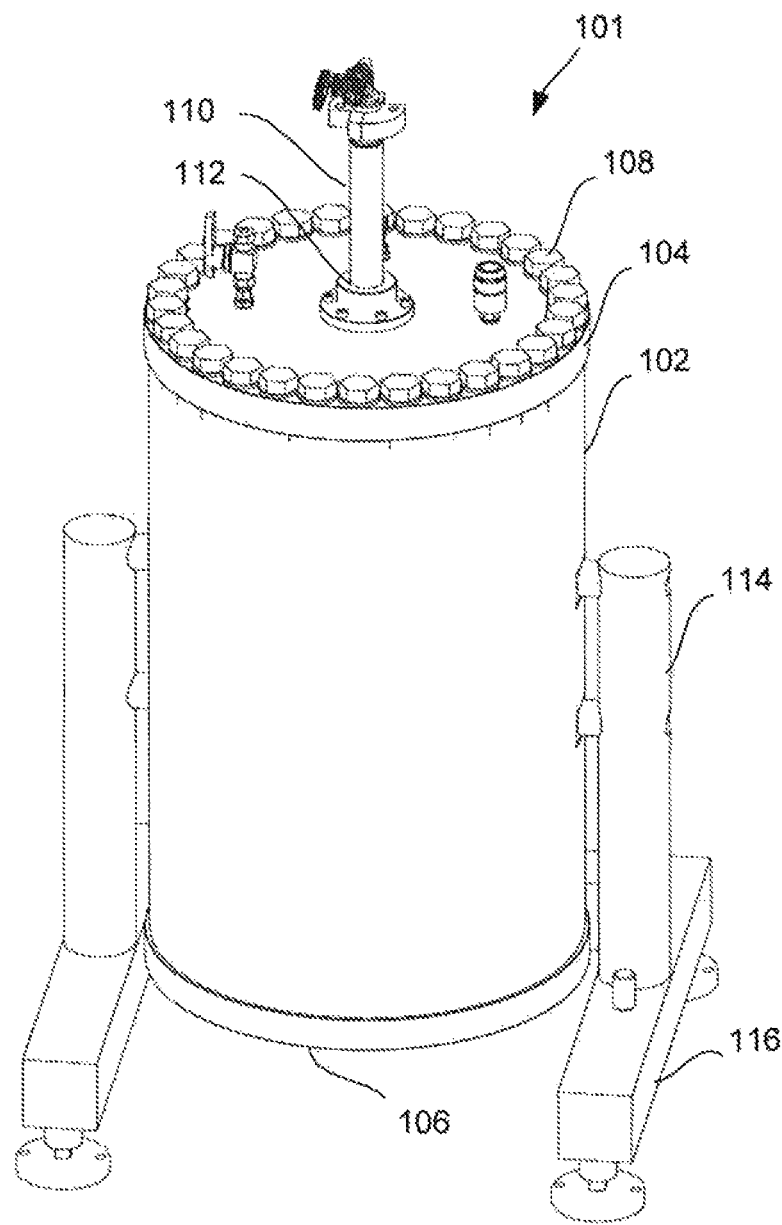
FIG. 1 shows a perspective view of a chromatography column according to an embodiment of the present invention.

FIG. 1 shows a view in perspective of a chromatography column 101 according to an embodiment of the present invention, which comprises a tubular housing 102, a first end unit 104 and a second end unit 106, secured together to form a fluid tight seal by means of tension bolts 108. The tubular housing 102 and end units 104, 106 may be composed of stainless steel or a high-strength plastic material such as polypropylene. In an embodiment, where the column 101 is to be used for the separation of biologically active substances, the material is biologically inert such that it does not elicit an immune response in humans in accordance with United States Pharmacopia (USP) <88> class VI. An adaptor rod 110 extends through an opening 112 in the first end unit 104 and into the tubular housing 102. The column 101 is arranged on a frame 114 provided with legs 116, so that the column 101 may be placed on a floor in a stable position.

Figure 2:
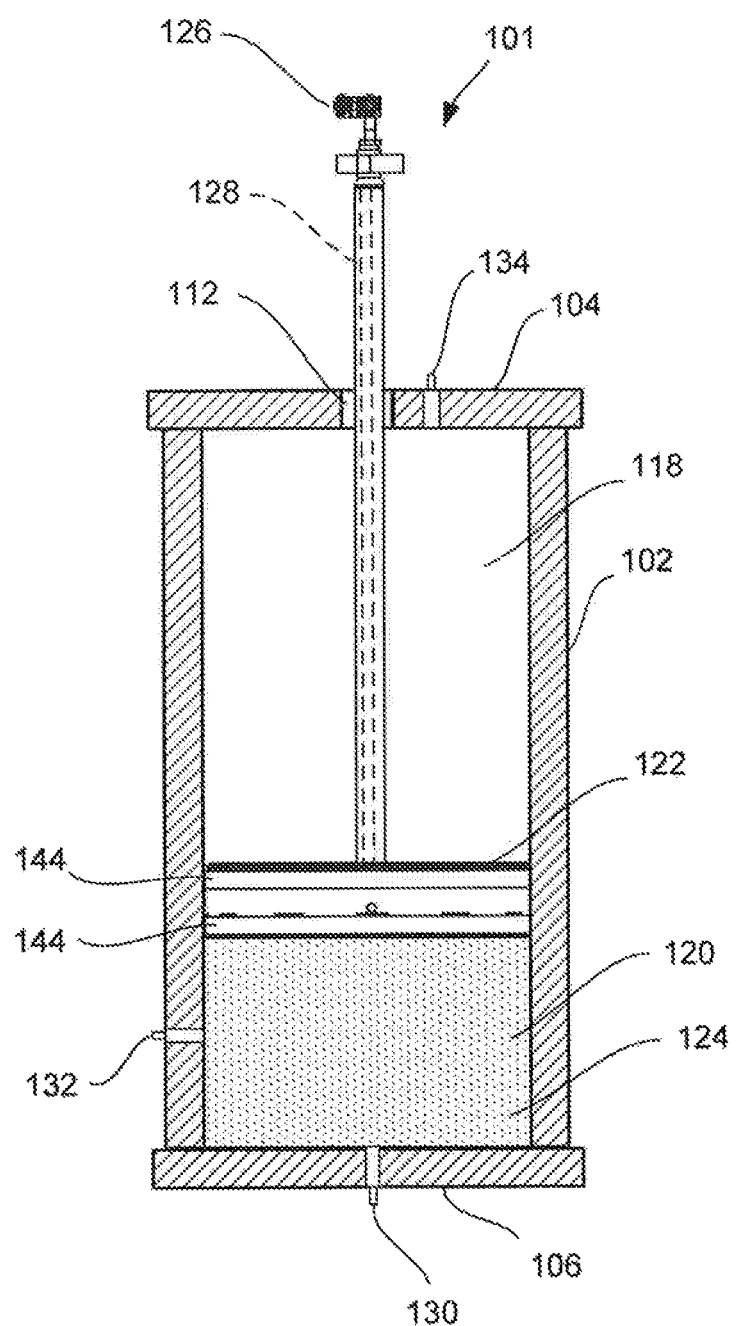
FIG. 2 shows a schematic section view of the chromatography column in FIG. 1.

FIG. 2 shows a schematic section view of the chromatography column 101 in FIG. 1. The tubular housing 102 and the end units 104, 106 form a fluid space 118 and bed space 120, which spaces both are fluid tight and are capable of withstanding high operating pressures. A wide range of column capacities is possible, ranging from 0.1 to 2000 liters.

The bed space 120 is defined by the tubular housing 102, the second end unit 106 and an adaptor 122 connected to the adaptor rod 110. The bed space 120 is filled with a bed 124 of packing material, which is usually particulate in nature and consists of a porous medium. A liquid mobile phase is arranged to enter through an inlet 126 at the end of the adaptor rod 110 and flows through a central channel 128 in the adaptor rod 110 and further to the adaptor 122. The liquid mobile phase thereafter moves through the bed 124 of packing material and is finally removed via an outlet 130 in the second end unit 106. The porous medium enclosed in the column 101 as a packed bed 124 may be formed by consolidating a suspension of discrete particles, known as slurry that is pumped, poured or sucked into the column 101 from a bore or nozzle 132 located at the tubular housing 102. It is also possible to supply the slurry to the bed space 120 through the central channel 128 in the adaptor rod 110.

The bed 124 of packed particulate medium is obtained by the downward movement of the adaptor 122 to compress the bed 124 between the adaptor 122 and the second end unit 106. The compression force and downward movement of the adaptor 122 is achieved by a pressurized fluid in the fluid space above the adaptor 122. The fluid, e.g. water, is pumped into the column 101 from a valve 134 located at the first end unit 104. It is also possible to move the adaptor downward to achieve a compression force to the bed 124 by forcing the adaptor rod 110 downward by means of a driving arrangement (not disclosed).

Figure 3:
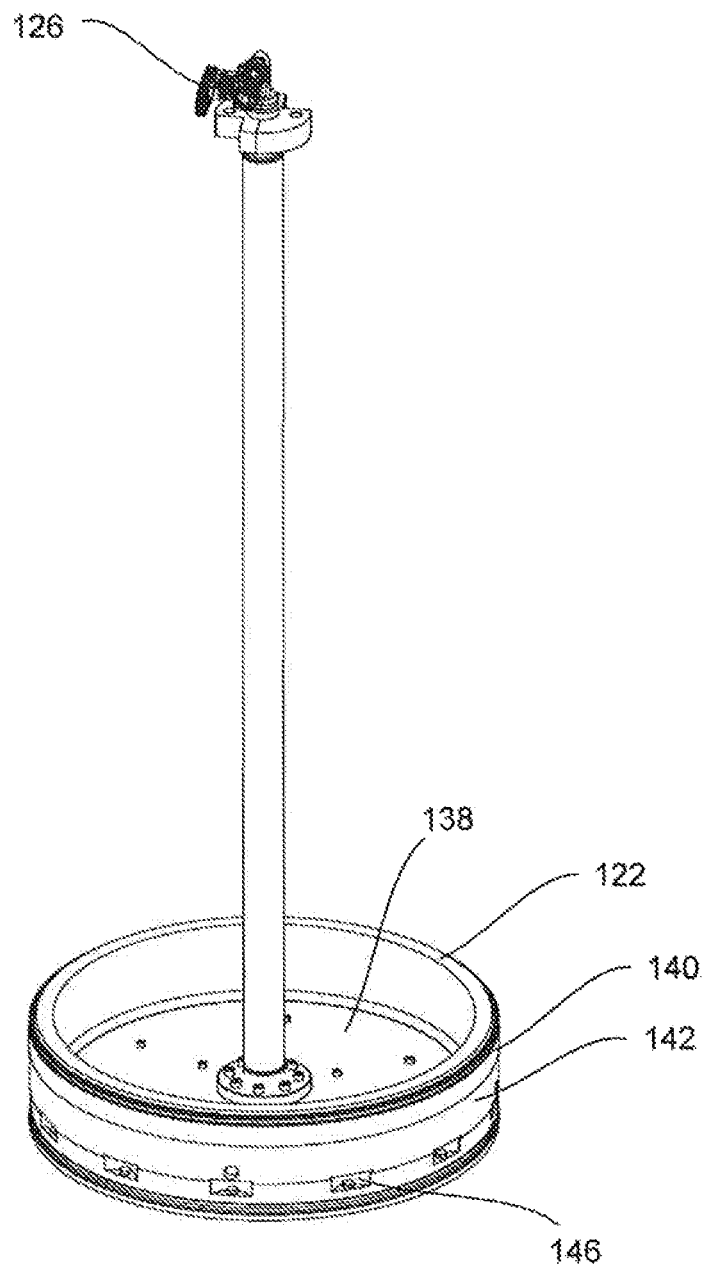
FIGS. 3, 4, 5, 6, and 7 show an adaptor assembly in different views according to an embodiment of the present invention.

FIG. 3 shows a view in perspective of an adaptor assembly 122, which is provided with a chromatography column filter 136. The adaptor 122 has a substantially circular shape provided with a bottom plate 138 on which a ring shaped wall element 140 is arranged. The peripheral outer surface 142 of the ring shaped wall element 140 is provided with sliding rings 144, which are arranged to seal against the inner surface of the tubular housing 102 of the chromatography column 101. The sliding rings 144 prevent leakage of fluid from the fluid space 118 to the bed space 120. The ring shaped wall element 140 has an essential extension in an axial direction of the adaptor 122. The axial extension of the ring shaped wall element 140 contributes to an axial stability of the adaptor 122 in the column 101, so that the surface of the bottom plate 138 always is parallel to the surface of the second end unit 106. As a result the compression of the packed bed 124 will be uniform, and the production of a stable, even bed 124 is often critical to the final separation process in the chromatography column 101. A number of cavities 146 are circumferentially and evenly arranged in the peripheral outer surface 142 of the ring shaped wall element 140 of the adaptor 122. The function of these cavities 146 will be described further below. The adaptor rod 110 may be removably connected to the adaptor 122 or attached to the adaptor 122 with a non removable connection.

Figure 4:
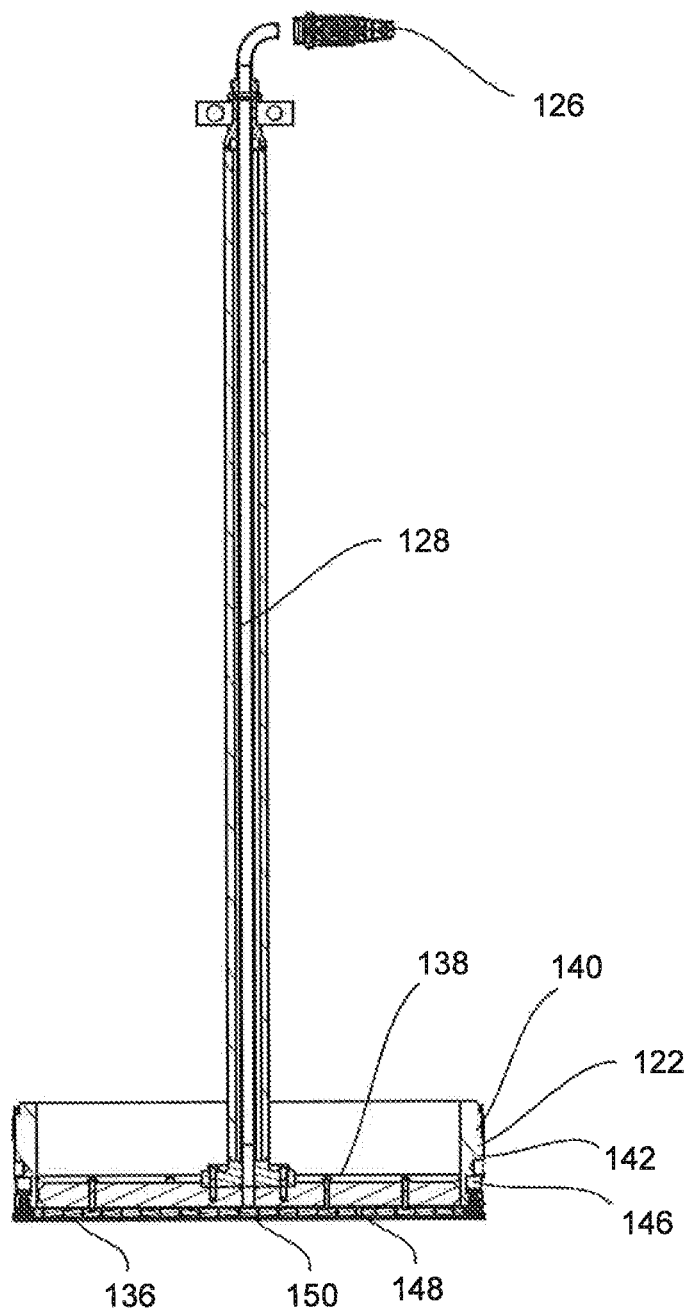
Figure 5:
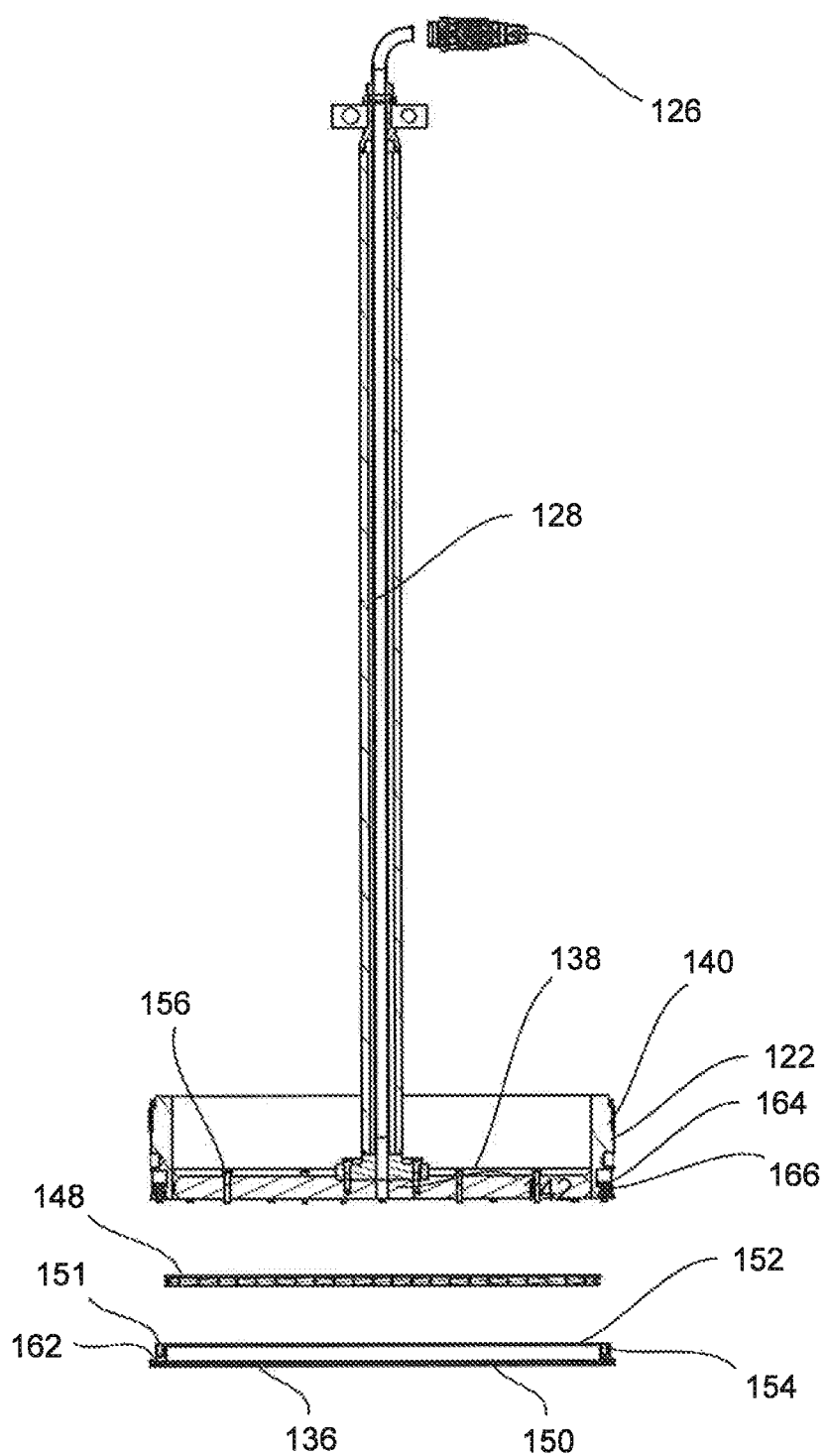
Figure 6:
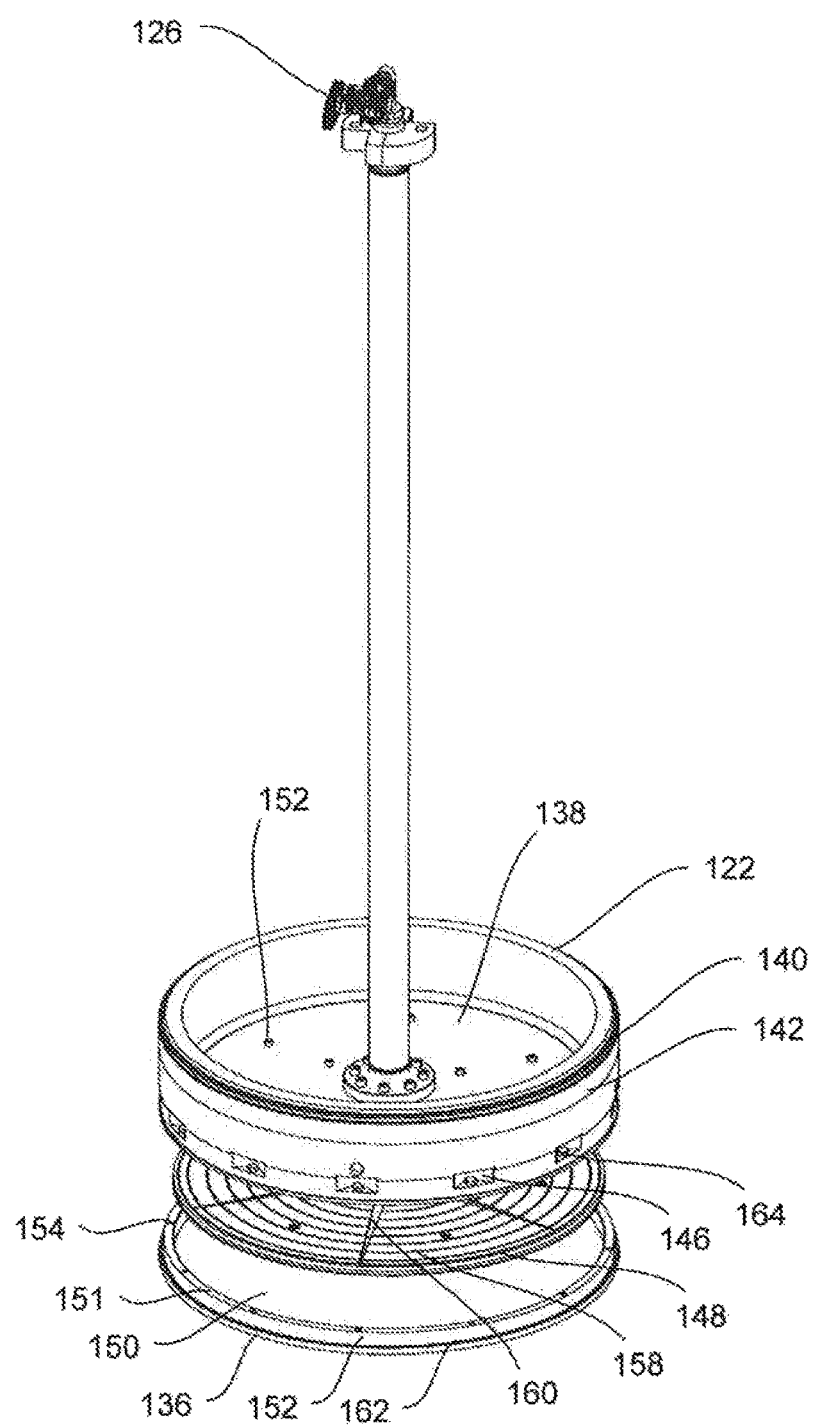

FIGS. 4 and 5 show section views of the adaptor 122 disclosed in FIG. 3. In FIG. 4 a distributor plate 148 and a chromatography column filter 136 are mounted on the adaptor 122. In FIG. 5 the distributor plate 148 and the filter 136 are separated from the adaptor 122. The chromatography column filter 136 comprising, a porous, perforated net element 150 through which fluid and particles up to a predetermined size are allowed to pass. A substantially circular, ring shaped fixating means 152 is attached to the net element 150. The fixating means 152 is provided with at least one fastening element 154, 254 for removably fixating the filter 136 to the adaptor 122 of the chromatography column 101, so that the filter 136 may be easy, fast and safe to replace. Also, the filter 136 is easy to clean when the filter 136 is removably fixated to the adaptor 122 by means of the fastening elements 154, 254.

A distributor plate 148 is removably connected to the bottom plate 138 of the adaptor 122 by means of fasteners 156. The distributor plate 148 comprises channels 158 arranged in a pattern to substantially uniform distribute the fluid over the plate 148. The distributor plate 148 is perforated with holes or openings 160 which lead the fluid from the channels 158 and uniformly into the packed bed 124. The filter 136 prevents particles from the bed 124 to enter into the holes or openings 160 within the distributor plate 148 and thereby preventing the particles from escaping the column.

The fastening element may be at least one threaded bore 154 in the fixating means 152. More particularly, several threaded bores 154 are evenly arranged in the ring shaped fixating means 152. Threaded bolts 164 are correspondingly arranged in the adaptor 122. The threaded bolts 164 removably fixate the fixating means 152 to the adaptor 122 and the removal of the threaded bolts 164 will make the replacement of the filter 136 easy, fast and safe. Each threaded bolt 164 is arranged in a cavity 146 in the periphery of the ring shaped wall element 140 of the adaptor 122. From each cavity 146 a bore 166 extends in an axial direction of the adaptor 122. The cavities 146 and bores 166 make it possible to connect the fixating means 152 by means of the threaded bolts 164 which extend through the axial directed bores 166. Each cavity 146 has a depth and an extension in the circumferential direction of the adaptor 122 large enough to reach the head of the threaded bolt 164 by means of a tool, for example a wrench.

The fastening element may also be several threaded pins 254 evenly arranged on the ring shaped fixating means 152. Nuts 168 are correspondingly arranged in the adaptor 122, so that removal of the nuts 168 will make the replacement of the filter 136 easy, fast and safe.

Figure 7:
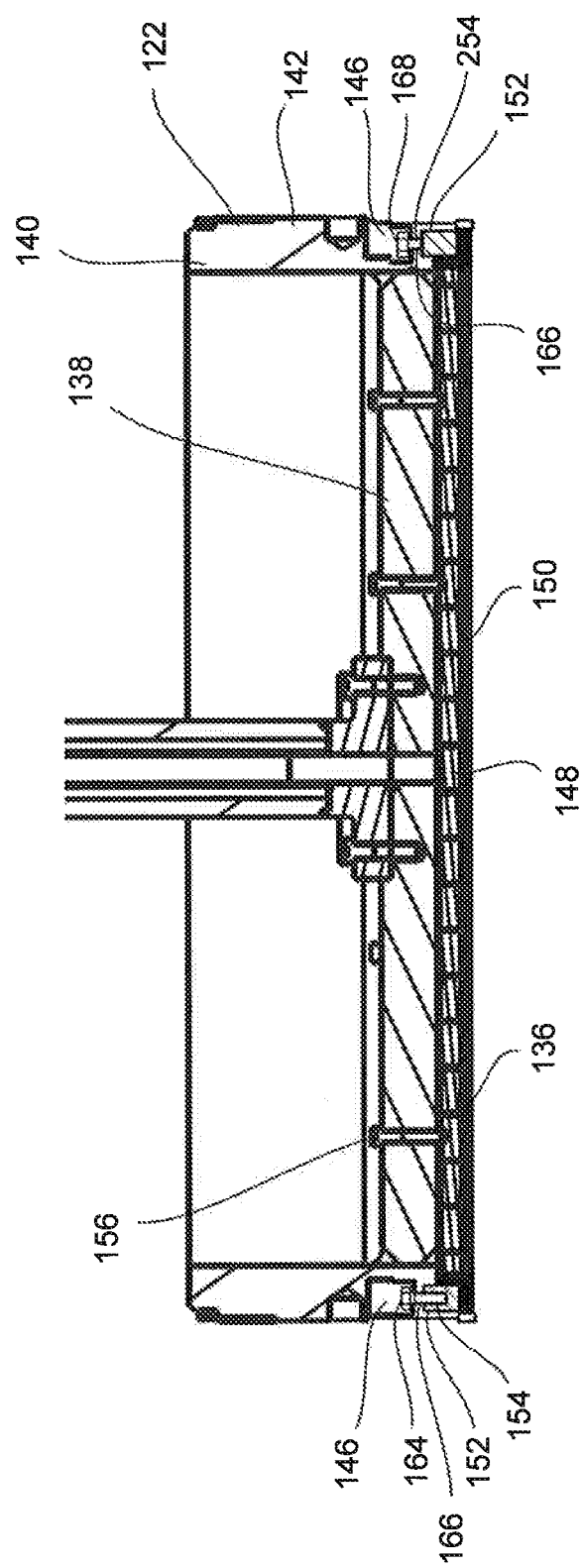

FIG. 7 shows a section view in detail of an adaptor 122 according to an embodiment of the invention. In FIG. 7 fastening elements 154, 254 of both alternatives are disclosed. On the left hand side in FIG. 7 the fastening element in the shape of a threaded bore 154 is disclosed. The threaded bore 154 is arranged in the fixating means 152 and a threaded bolt 164 fixates the fixating means 152 to the adaptor 122. On the right hand side in FIG. 7 the fastening element in the shape of a threaded pin 254 is disclosed. The threaded pin 254 is arranged on the fixating means 152 and a nut 168 fixates the fixating means 152 to the adaptor 122. The cavities 146 arranged in the ring shaped wall element 140 of the adaptor 122 are clearly disclosed. As mentioned above, the cavities 146 are circumferentially arranged in the periphery of the ring shaped wall element 140 and make it possible to arrange the threaded bolt 164 or nut 168 through the axial directed bores 166 in the adaptor 122. When mounted in the chromatography column 101 the cavities 146 are substantially covered by one of the sliding rings 144, disclosed in FIG. 2.

Figure 8:
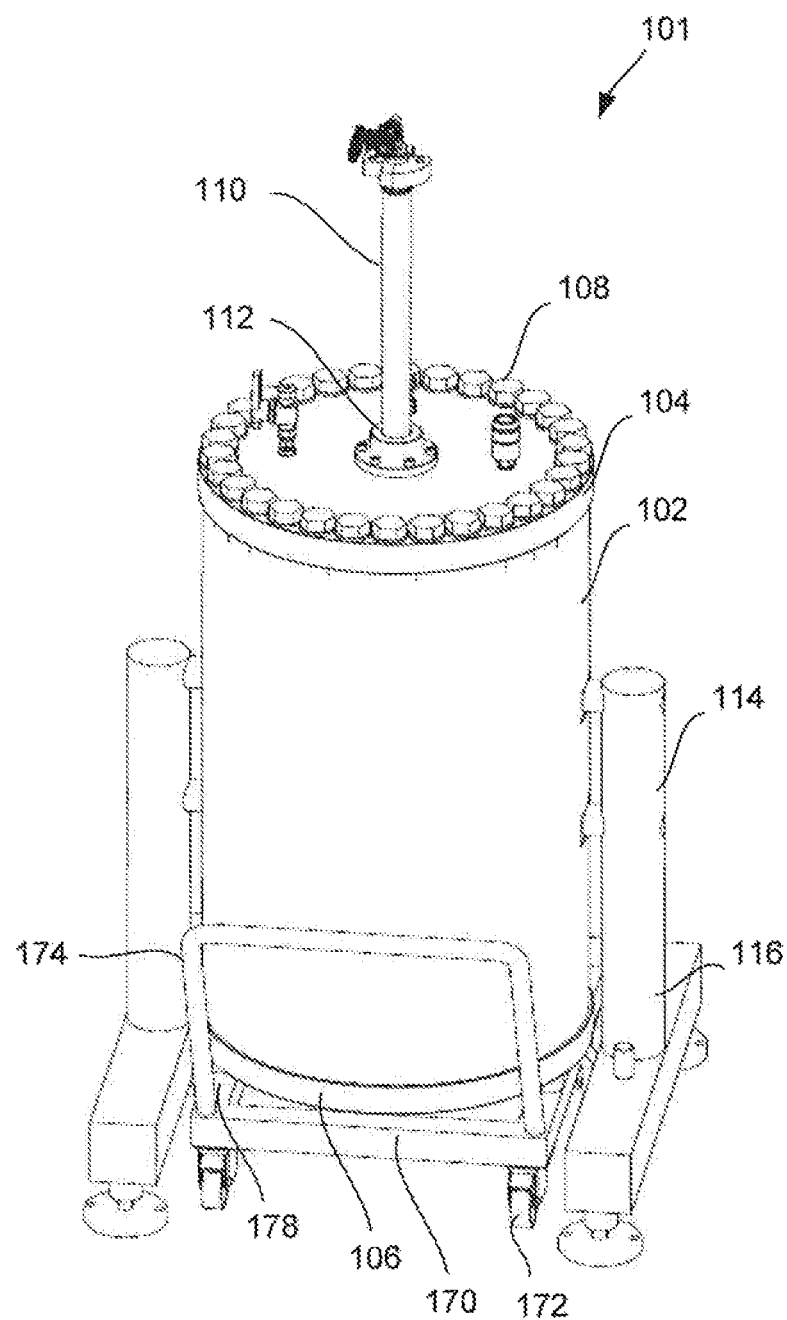
FIG. 8 shows a view in perspective of the chromatography column in FIG. 1 with a support trolley positioned under the column.
Figure 9:
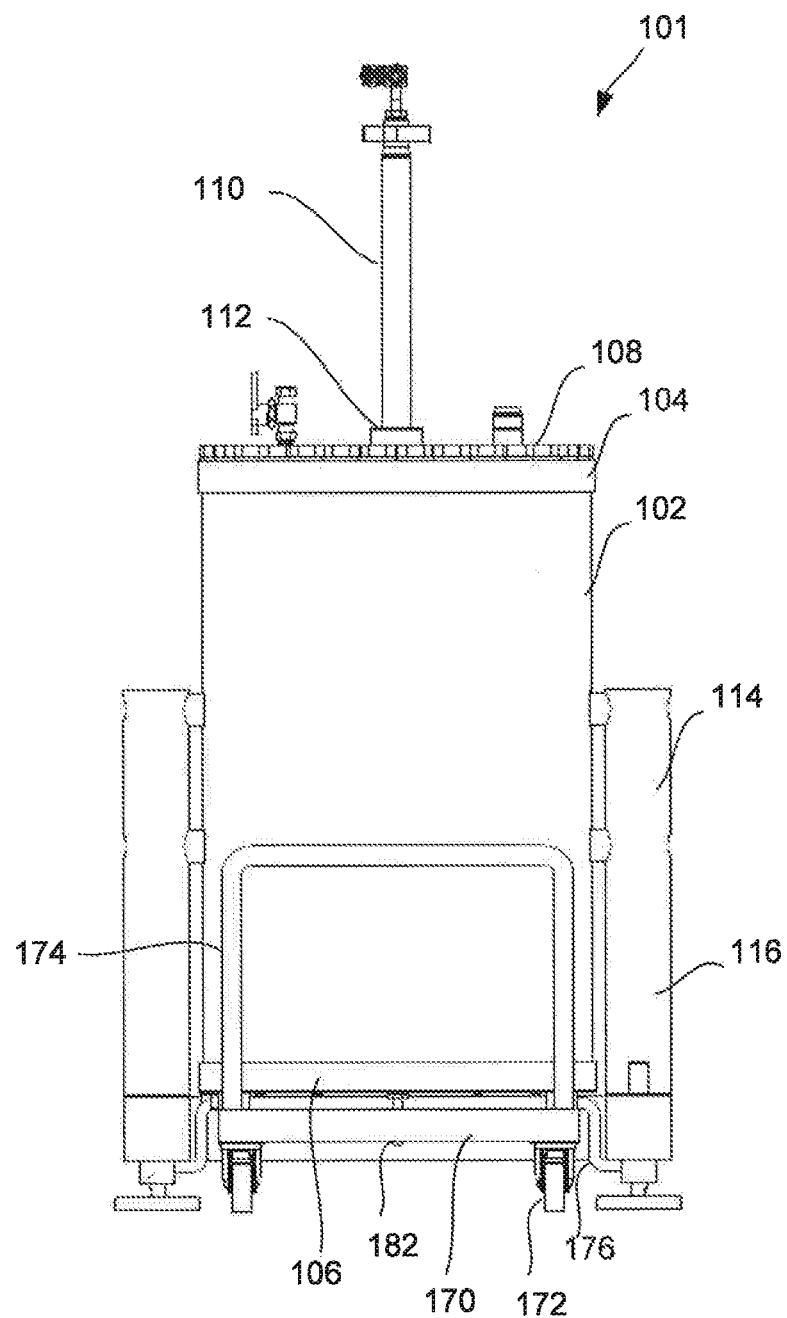
FIG. 9 shows a side view of the chromatography column in FIG. 8.

FIG. 8 and FIG. 9 shows a first step of a method of conducting maintenance on the chromatography column 101 according to an embodiment of the invention. A support trolley 170 is provided in a position under the column 101. The trolley 170 is provided with wheels 172 and a handle 174 for easy moving the trolley 170 by an operator. Also, the trolley 170 is provided with a locking mechanism 176 for locking and securing the trolley 170 to the frame, so that the trolley 170 is prevented from moving substantially vertically. It is also possible to arrange the locking mechanism 176 on the frame 114. More particularly, the locking mechanism 176 is a pair of curved consoles, which abut under the frame 114 and above the trolley 170. The trolley 170 is also provided with a support surface 178 on which different parts of the chromatography column 101 may rest.

Before the trolley 170 has been provided under the chromatography column 101 tension bolts 180 which connect the second end unit 106 to the tubular housing 102 must be removed. In order to get access to the tension bolts 180, in the space between the second end unit 106 and the floor, the entire chromatography column 101 may be lifted substantially vertically by actuators 180 arranged on the frame 114.

Figure 10:
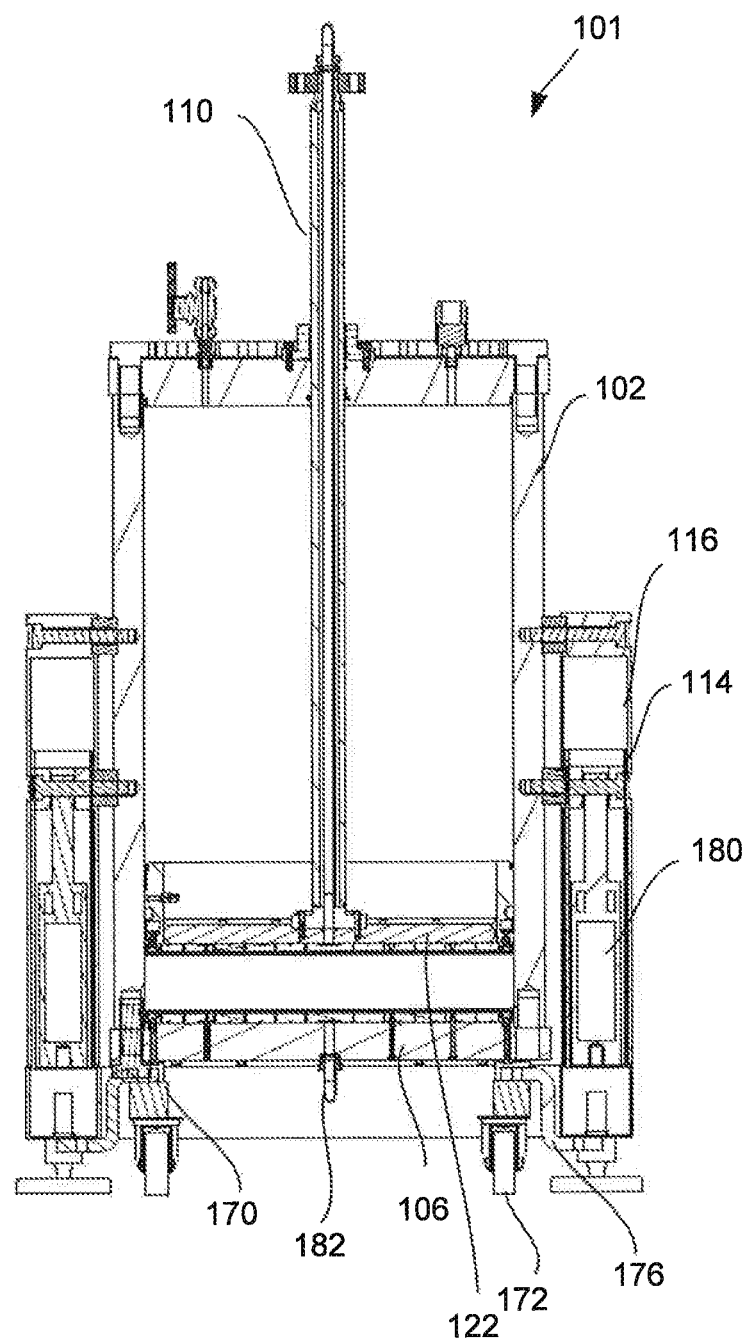
FIG. 10 shows a section view of the frame connected to the chromatography column according to an embodiment of the present invention.

FIG. 10 shows a cross section view of the chromatography column 101 provided with the frame 114 and the support trolley 170 arranged in a position under the chromatography column 101. More particularly, the actuating means 180 are hydraulic cylinders 180 arranged in each leg 116 of the frame 114. However, instead of or in combination of, the actuating means 180 may also be pneumatic cylinders or electrical motors arranged in each leg 116 of the frame 114.

When the support trolley 170 is arranged in a position under the chromatography column 101, the column 101 is lowered by means of the hydraulic cylinders 180 arranged in the legs 116 of the frame 114, so that the second end unit 106 of the chromatography column 101 rests on the trolley 170. Although the tension bolts 108 connecting the second end unit 106 to the tubular housing 102 are removed the second end unit 106 may not be separated from the tubular housing 102 without a substantial force. This is because of frictional forces and tolerances between the second end unit 106 and the tubular housing 102. Therefore, the second end unit 106 to the trolley 170 may be connected by means of at least one fastening element 182, for example a threaded bolt. The threaded bolt may be arranged through a bore in the support surface 178 of the trolley 170 and in to a threaded bore in the second end unit 106.

Figure 11:
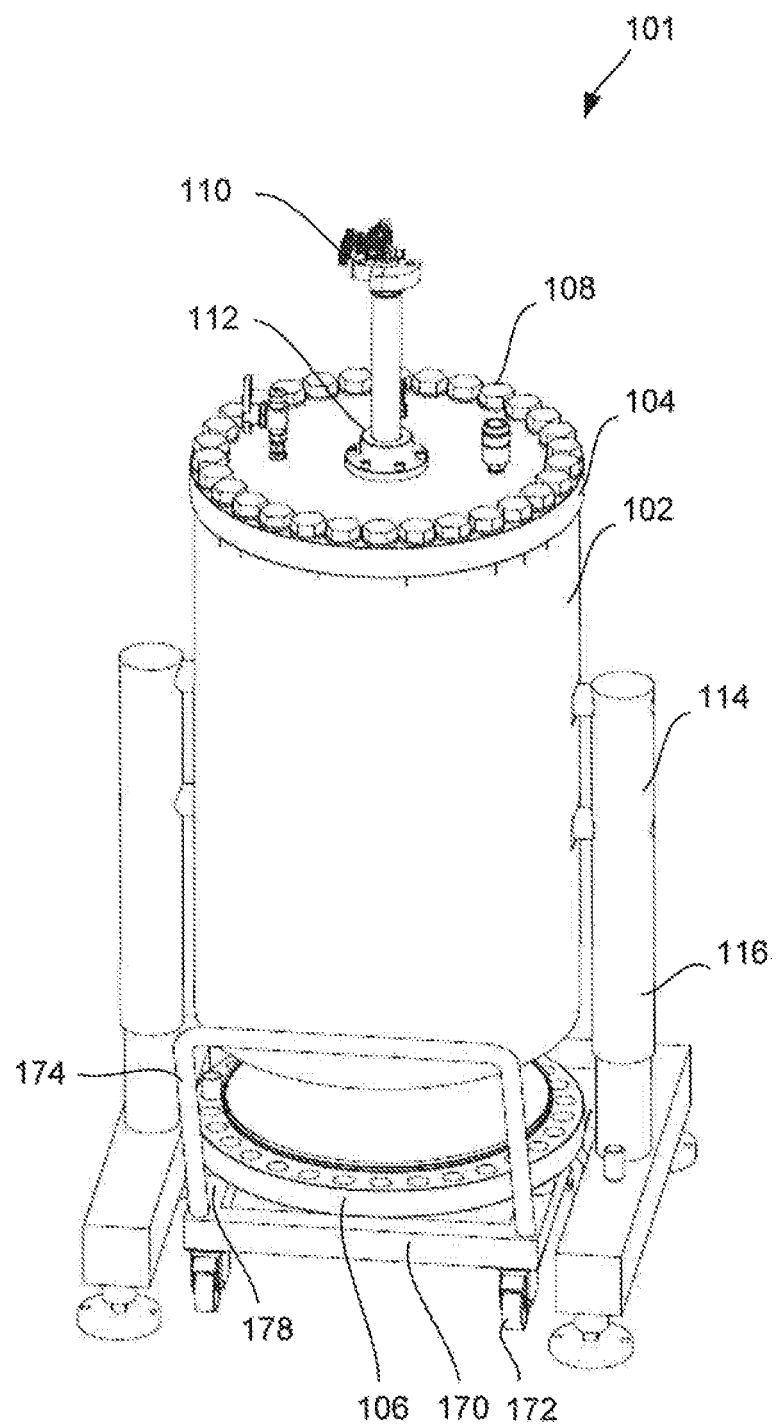
FIG. 11 shows a view in perspective of the chromatography column in FIG. 8 lifted by the frame.

FIG. 11 shows how the column has been lifted substantially vertically by means of the hydraulic cylinders 180 on the frame 114, so that the second end unit 106 has been separated from the tubular housing 102 of the column 101. The locking mechanism 176 prevents lifting of the trolley 170 from the floor when the second end unit 106 is secured on the trolley 170. On the second end unit 106 a filter 136 and a distributor plate 148 are arranged.

Thereafter the trolley 170 together with the second end unit 106 is withdrawn from the frame 114 and the second end unit 106 is released from the trolley 170 by removing the threaded bolt 182, which connects the second end unit 106 to the trolley 170. The second end unit 106 may thereafter be displaced to a maintenance area for replacing or cleaning the filter 136.

Figure 12:
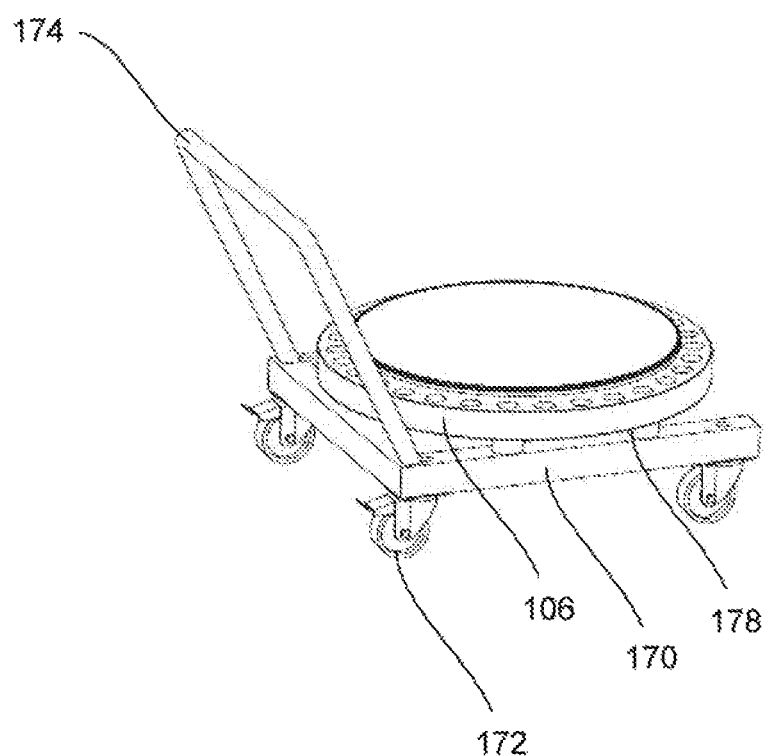
FIG. 12 shows a view in perspective of the support trolley together with the second end unit resting on the trolley according to an embodiment of the present invention.

In FIG. 12 the second end unit 106 is disclosed resting on the trolley 170. Because the trolley 170 is provided with wheels 172 and a handle 174 it is easy to withdraw the trolley 170 from the frame 114. Also, when the trolley 170 is withdrawn from the frame 114 the trolley 170 is automatically disconnected from the locking mechanism 176.

Figure 13:
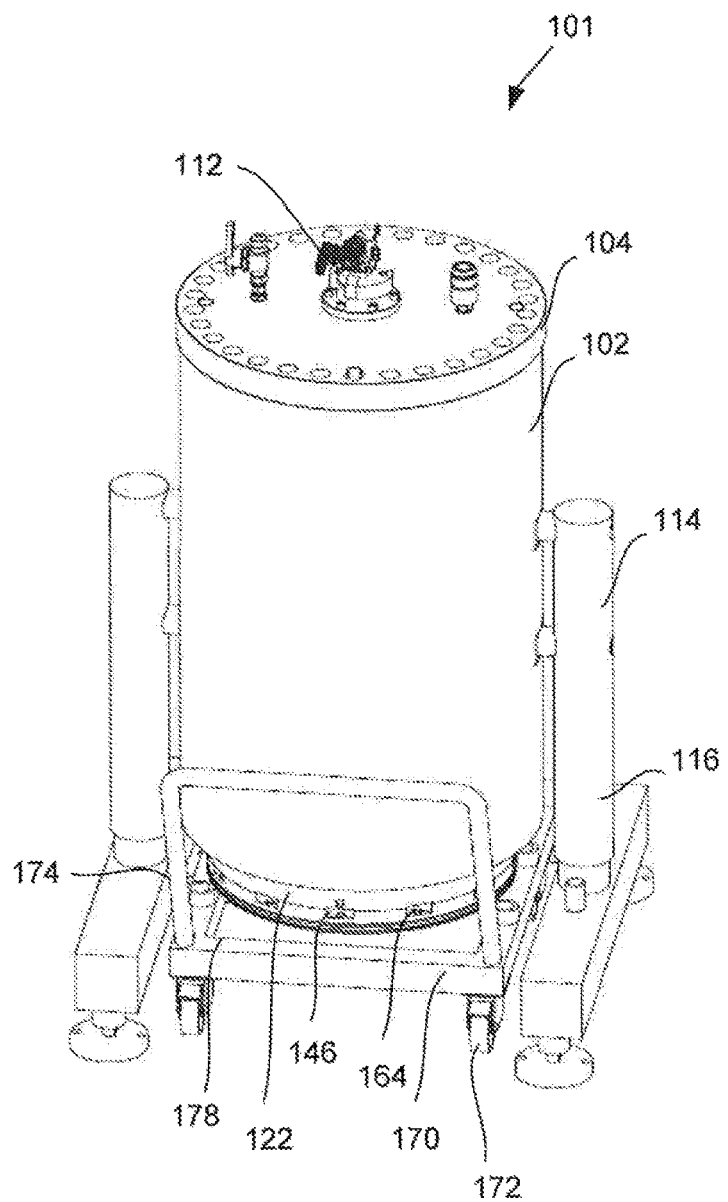
FIG. 13 shows a view in perspective of the chromatography column with the adaptor assembly in a first lowered adaptor position according to an embodiment of the present invention.

In order to remove the filter 136 from the adaptor assembly 122, the adaptor assembly 122 is lowered within the column 101 to a first lowered adaptor position by means of the adaptor rod 110. In FIG. 13 the trolley 170 has been replaced under the column 101 and it is possible to lower the column 101 by means of the hydraulic cylinders 180 so that the filter 136 of the adaptor assembly 122 rests on the support surface 178 of the trolley 170. However, when the adaptor assembly 122 is in the first lowered adaptor position it may be possible to remove the filter 136 without the use of the trolley 170. This is dependent of the weight of the filter 136.

In the first lowered adaptor position a part of the adaptor assembly 122 is still within the tubular housing 102 of the column 101, so that the compression fluid held within the column 101 above the adaptor assembly 122 cannot escape from the column 101. More particularly, in the first lowered adaptor position 122 the first sliding ring 144 of the adaptor assembly 122 is positioned to rest on an inner surface of the tubular housing 102 in order to provide a tight seal between the adaptor assembly 122 and the tubular housing 102. In the first lowered adaptor position the cavities 146 arranged in a periphery of the adaptor assembly 122 are positioned outside the tubular housing 102, so that it is possible to get access to the cavities 146 from outside of the column 101 after removing the second sliding ring 144, which covers the cavities 146. Thereafter the fastening means 164,168 are released trough the cavity 146 for removing the filter 136 from the adaptor assembly 122.

Figure 14:
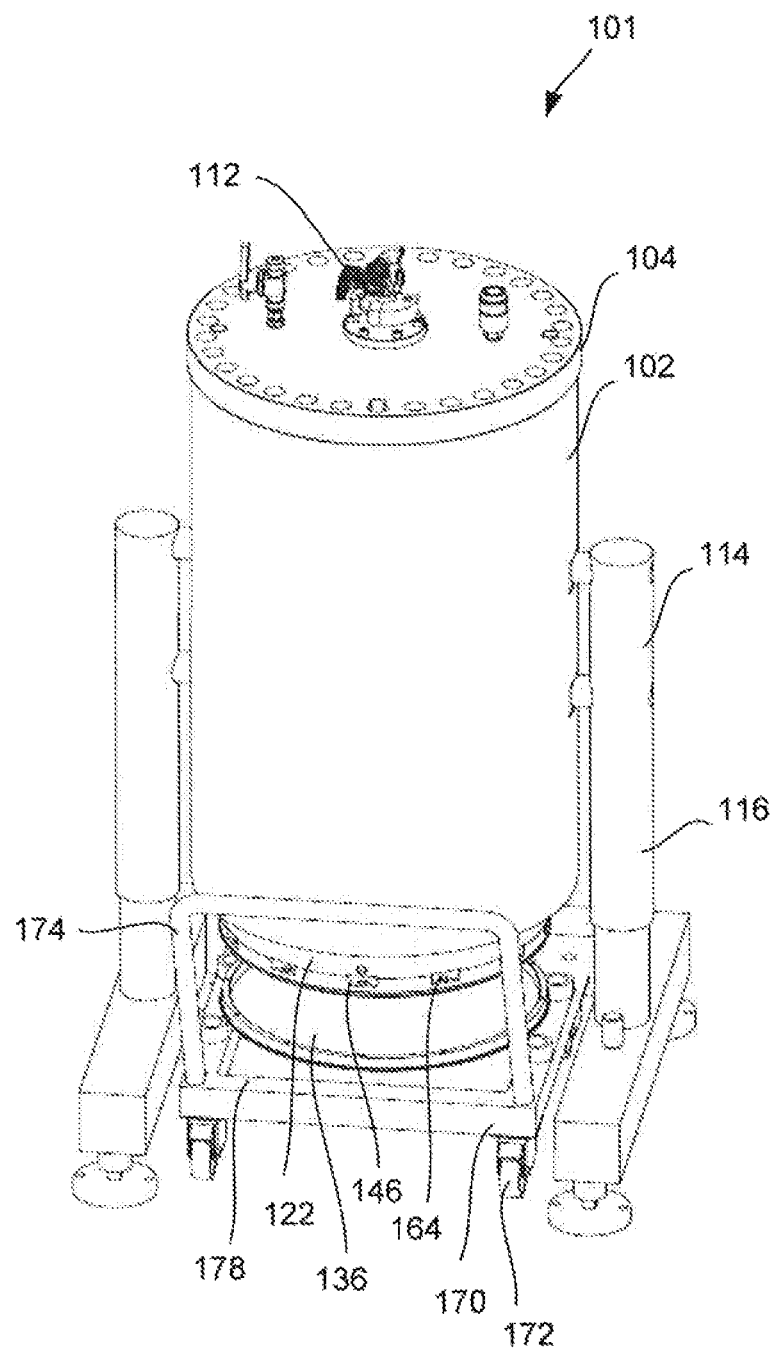
FIG. 14 shows a view in perspective of the chromatography column with the filter removed from the adaptor assembly according to an embodiment of the present invention.

FIG. 14 shows the filter 136 removed from the adaptor assembly 122 and resting on the support trolley 170 after lifting the column 101 substantially vertically by means of the hydraulic cylinders 180 on the frame 114. When lifting the column 101 the filter 136 will be separated from the adaptor 122 and rest on the support surface 178 of the trolley 170. Thereafter, the trolley 170 is withdrawn from the frame 114 and displaced to the maintenance area for replacing or cleaning the filter 136. Instead of removing the filter 136 from the adaptor assembly 122 the filter 136 may be cleaned when mounted on the adaptor assembly 122. Therefore, if the filter 136 should not be removed from the adaptor assembly 122 at this stage it is not necessary to provide the adaptor assembly 122 with cavities 146 in the periphery of the ring shaped wall element 140 of the adaptor 122.

If also the adaptor assembly 122 should be removed, any compression fluid above the adaptor 122 should be removed trough a draining valve in the adaptor or by means of suction valve in the tubular housing 102. Thereafter, the support trolley 170 is replaced in a position under the column 101 and the adaptor assembly 122 is lowered to a second lowered adaptor position by means of the adaptor rod 110.

Figure 15:
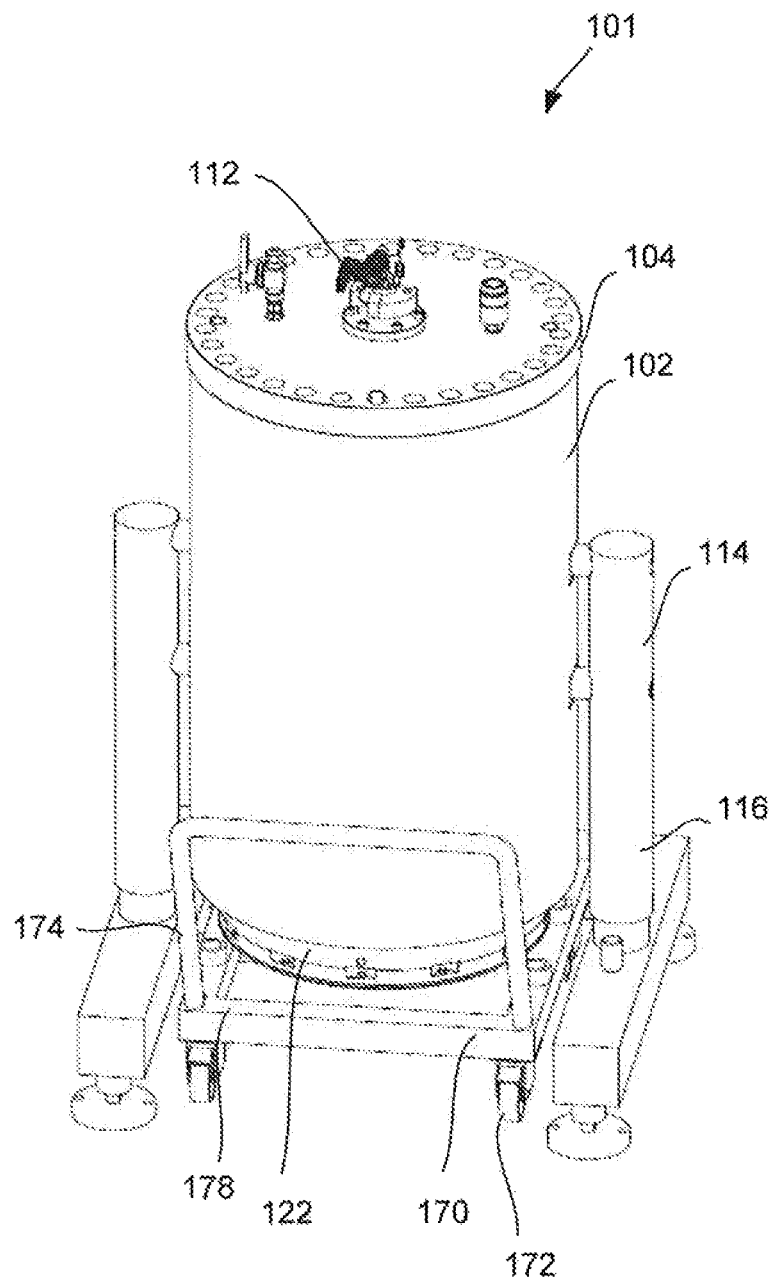
FIG. 15 shows a view in perspective of the chromatography column with the trolley replaced under the column and with the adaptor assembly in the first lowered adaptor position according to an embodiment of the present invention.

Alternatively, as disclosed in FIG. 15, the column 101 is lowered by the hydraulic cylinders 180 on the frame 114, so that the adaptor assembly 122 rests on the trolley 170 in the first lowered adaptor position and thereafter the column 101 is lifted by means of the hydraulic cylinders 180 on the frame 114 so that the adaptor assembly 122 is positioned in the second lowered adaptor position.

Figure 16:
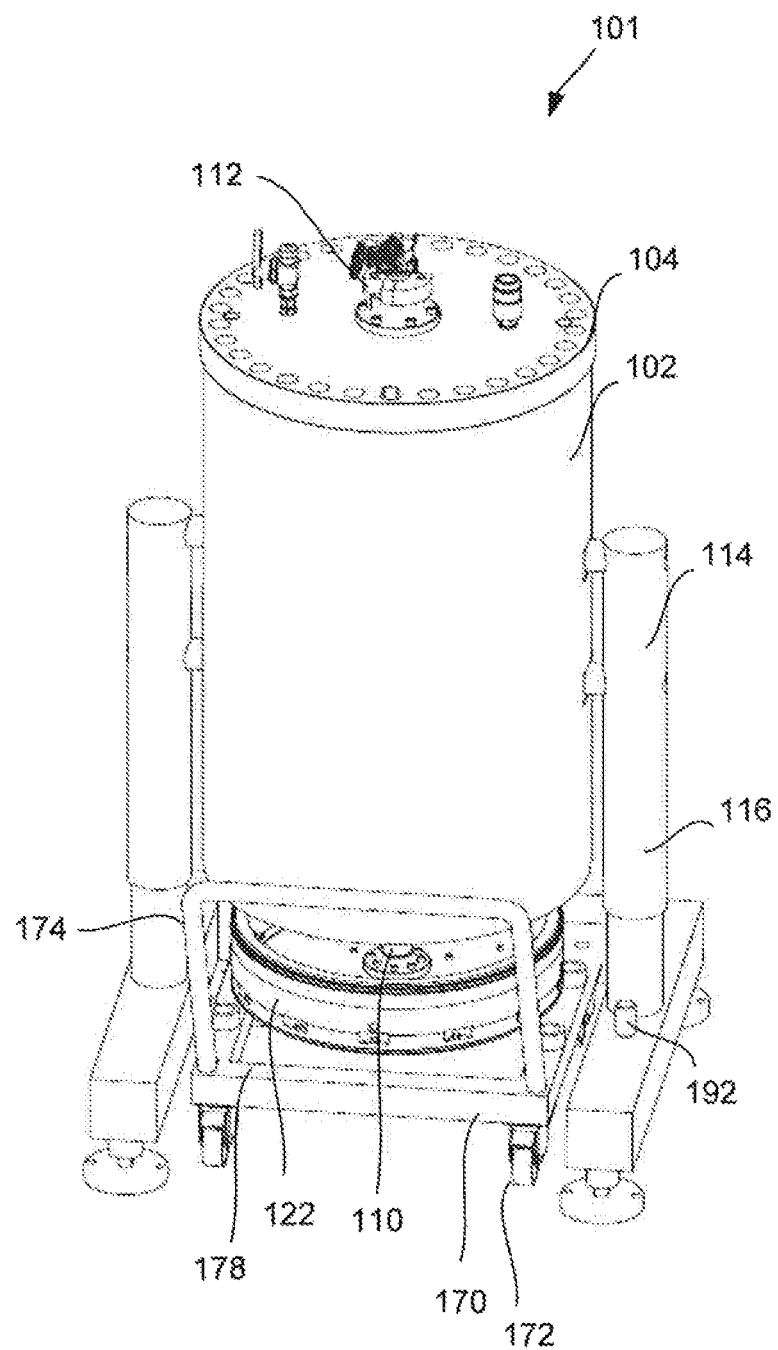
FIG. 16 shows a view in perspective of the chromatography column with the adaptor assembly in a second lowered adaptor position according to an embodiment of the invention.

In FIG. 16 the adaptor assembly 122 is positioned in the second lowered adaptor position. In this second lowered adaptor position access to the area above the adaptor 122 is possible, so that the adaptor 122 may be removed from the adaptor rod 110. After the adaptor 122 has been removed from the adaptor rod 110, the adaptor rod 110 is lifted or the column 101 is lifted by means of the actuating means 180 substantially vertically, so that the trolley 170 and the adaptor assembly 122 may be withdrawn from the frame 114 and displaced to the maintenance area. If the adaptor rod 110 and the adaptor assembly 122 cannot be dismounted from each other it may be possible to arrange the cylinders 180 with such dimensions that the tubular housing 102 may be lifted above the adaptor rod 110.

If also the first end unit 104 should be removed, the tension bolts 108 which connect the first end unit 104 to the tubular housing 102 must be released and removed.

Figure 17:
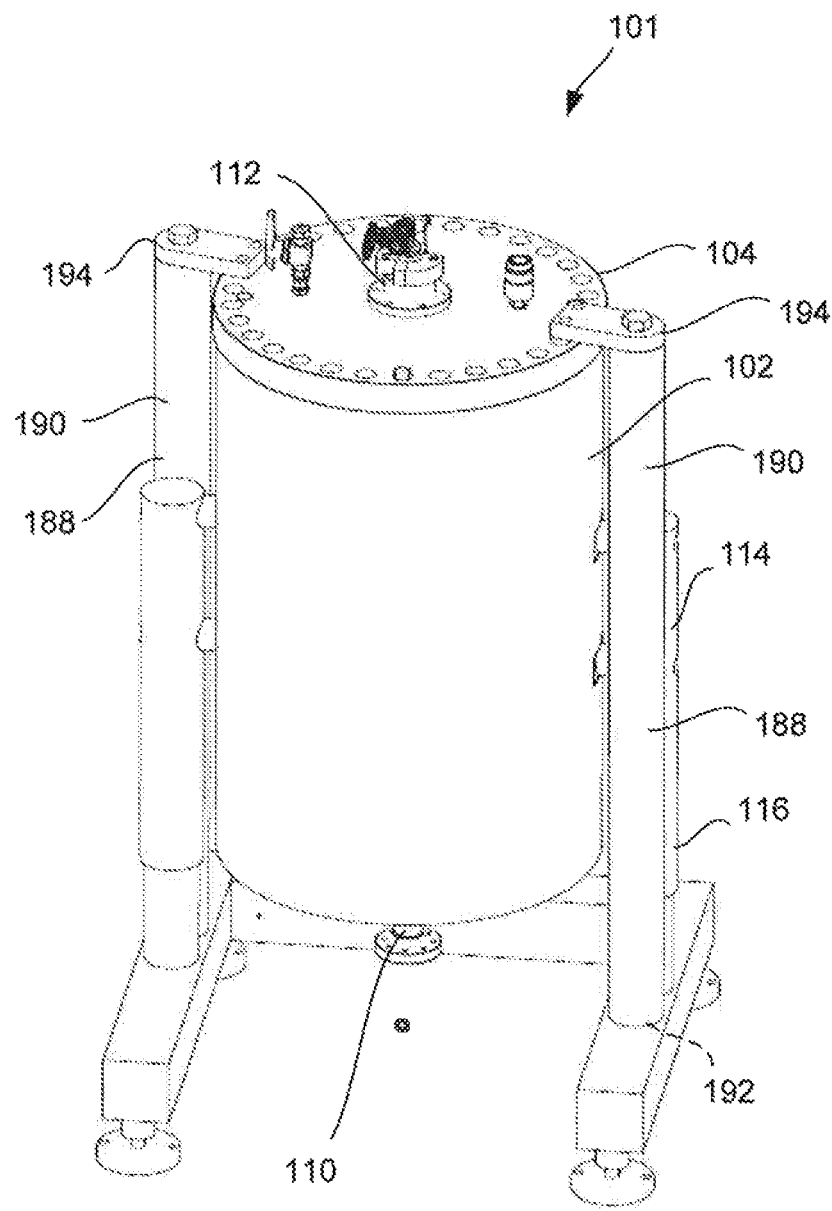
FIG. 17 shows a view in perspective of the chromatography column with a fixture means arranged on the first end unit and on the frame according to an embodiment of the invention.

FIG. 17 shows how a fixture means 188 has been arranged on the frame 114. The fixture means 188 comprises a pair of rods 190 which are connected to respective connecting pins 192 arranged on the frame 114. A bracket 194 is arranged on the top of each rod 190 and the brackets 194 connect the fixture means 188 to the first end unit 104 by means of bolts.

Figure 18:
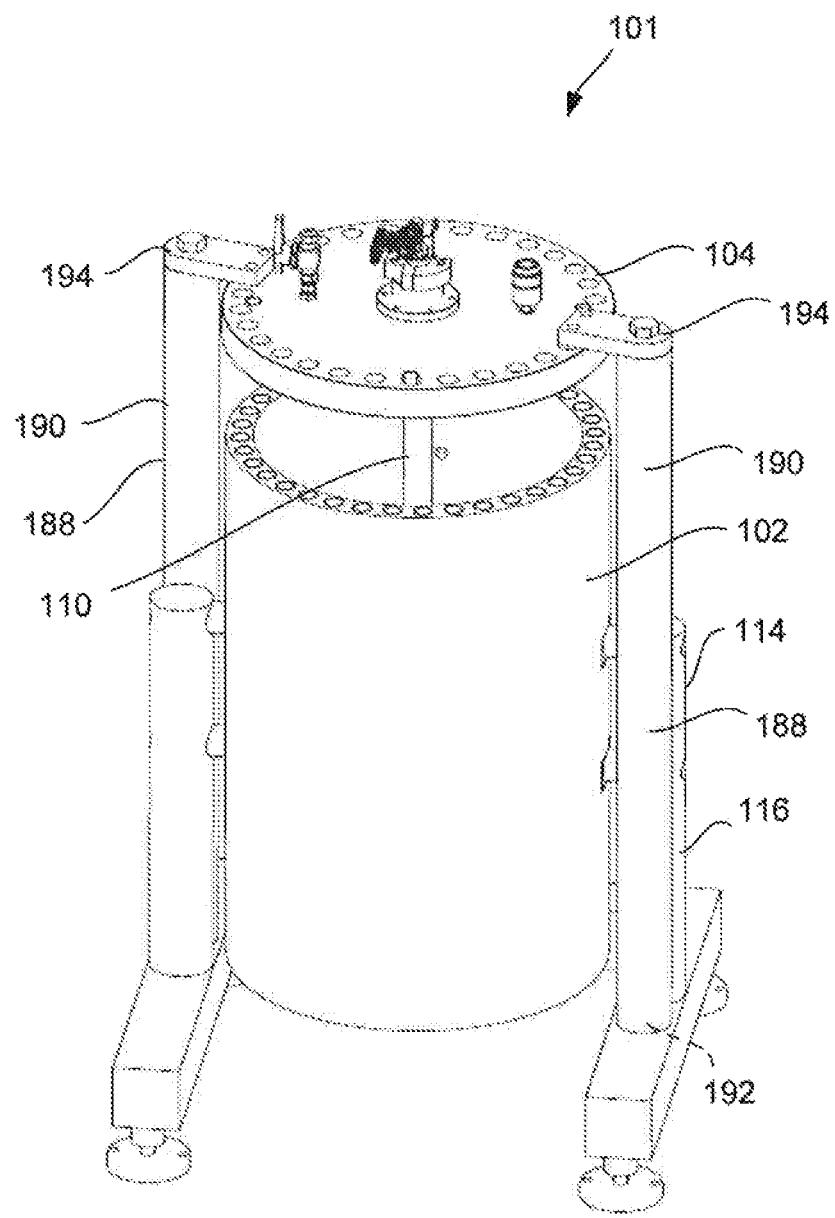
FIG. 18 shows a view in perspective of the chromatography column with the first end unit separated from the tubular housing according to an embodiment of the invention.

When lowering the column 101 substantially vertically by means of the actuating means 180 on the frame 114, the first end unit 104 is separated from the tubular housing 102, as disclosed in FIG. 18. Maintenance of the first end unit 104 and also the tubular housing 102 is now possible to perform.

As an alternative embodiment to the rod shaped fixture means 188 in FIGS. 17 and 18 it is also possible to provide the fixture means 188 a separate unit positioned directly on the floor. After the separation of the first end unit 104 from the tubular housing 102 the fixture means 188 and the first end unit 104 may be withdrawn from the frame 114 and the first end unit 104 may be displaced to the maintenance area.

In all embodiments described above parts and surfaces being in contact with a process fluid are suitably selected from materials that are in accordance with material requirements in (bio-)pharmaceutical manufacturing or food grade quality.

For example, materials are suitably in compliance with USP Class VI and 21 CFR 177. Furthermore they are suitably of animal-free origin and compliance to EMEA/ 410/01.

Features and components of the different embodiments above may be combined within the scope of the invention.

The invention claimed is:

1. A chromatography column comprising:
    a tubular housing having a side wall, the tubular housing suitable for holding a porous chromatographic medium;
    a first end unit removably connected to a first end of the tubular housing;
    a second end unit removably connected to a second end of the tubular housing;
    a circular adaptor assembly sealingly movable within said tubular housing;
    an adaptor rod connected to the center of said circular adaptor assembly, and arranged to extend through an opening in the first end unit;
    a filter removably connected to the adaptor assembly; and
    a frame comprising two legs, with each of the two legs connected to the side wall of said tubular housing for supporting the column on a floor,
    wherein at least one actuator is arranged on the frame, so that the tubular housing can be lifted and lowered in a substantially vertical direction to respectively disconnect thus expose or connect thus engage the second end unit.

2. The chromatography column of claim 1, wherein the at least one actuator is a hydraulic cylinder arranged in each of the two legs of the frame.

3. The chromatography column of claim 1, further comprising a fixing device removably arranged on the frame, and connectable to the first end unit to hold the first end unit independently from the tubular housing and the two legs of the frame.

4. The chromatography column of claim 3, wherein the fixing device comprises a pair of rods provided with a bracket arranged on the top of each rod for connecting the rods to the first end unit via bolts.

5. The chromatography column of claim 1, wherein the adaptor rod is removably connected to said adaptor assembly.

6. The chromatography column of claim 1, further comprising a first sliding ring of the adaptor assembly positioned to rest on an inner surface of the tubular housing in order to provide a tight seal between the adaptor assembly and the tubular housing.

7. The chromatography column of claim 6, wherein when the adaptor assembly is lowered to a first lowered adaptor position via the adaptor rod, the adaptor assembly being within the tubular housing of the column, so that a compression fluid held within the column above the adaptor assembly cannot escape from the column.

8. The chromatography column of claim 1, wherein the adaptor assembly is provided with at least one cavity arranged in a periphery of the adaptor assembly, and in which a fastener is arranged to connect the filter to the adaptor assembly.

9. The chromatography column of claim 8, further comprising a second sliding ring that covers the at least one cavity.

10. The chromatography column of claim 1, further comprising a trolley having a support surface for the second end unit to rest on when the column is lifted substantially vertically so that the second end unit is separated from the tubular housing of the column, wherein the trolley can be removed together with the second end unit from the frame.

11. The chromatography column of claim 10, wherein the second end unit is connected to the trolley via at least one fastening element.

12. The chromatography column of claim 10, further comprising a locking mechanism to secure the trolley to the frame to prevent the trolley from moving substantially vertically.

13. A chromatography column comprising:
a tubular housing having a cylindrical side wall, a first end, and a second end that is opposite the first end;
a first end unit removably connected to the first end;
a second end unit removably connected to the second end;
an adaptor assembly movable within said tubular housing along the cylindrical side wall and removable through the second end of the tubular housing;
an adaptor rod connected to said adaptor assembly, and arranged to extend through an opening in the first end unit;
a filter removably connected to the adaptor assembly; and
a frame that comprises two legs, which are connected to the side wall of said tubular housing for supporting the column on a floor with at least one hydraulic cylinder arranged in each leg of the frame as an actuator, so that the tubular housing can be lifted and lowered in a substantially vertical direction to respectively disconnect thus expose or connect thus engage the second end unit, and
a trolley having a support surface for the second end unit to rest on when the column is lifted substantially vertically so that the second end unit is separated from the tubular housing of the column, wherein the trolley can be removed together with the second end unit from the frame,
wherein, when the second end unit is released and removed from the trolley, the adaptor assembly can be lowered to a second lowered adaptor position via the adaptor rod, such that the adaptor assembly rests on the support surface of the trolley and access to the area above the adaptor is possible and the filter is exposed through the second end of the tubular housing.

14. The chromatography column of claim 13, further comprising a first sliding ring of the adaptor assembly positioned to rest on an inner surface of the tubular housing in order to provide a tight seal between the adaptor assembly and the tubular housing.

15. The chromatography column of claim 14, wherein when the adaptor assembly is lowered to a first lowered adaptor position via the adaptor rod, the adaptor assembly being within the tubular housing of the column, so that a compression fluid held within the column above the adaptor assembly cannot escape from the column.

16. The chromatography column of claim 13, wherein the adaptor assembly is provided with at least one cavity arranged in a periphery of the adaptor assembly, and in which a fastener is arranged to connect the filter to the adaptor assembly.

17. The chromatography column of claim 16, further comprising a second sliding ring that covers the at least one cavity.

18. The chromatography column of claim 13, wherein when the column is lifted substantially vertically by the frame, the second end unit can be separated from the tubular housing of the column to rest on the trolley and removed together with the trolley, wherein the second end unit is optionally connected to the trolley via at least one fastening element.

19. The chromatography column of claim 13, further comprising a locking mechanism to secure the trolley to the frame to prevent the trolley from moving substantially vertically.

20. The chromatography column of claim 13, further comprising a fixing device removably arranged on the frame, and connectable to the first end unit to hold the first end unit independently from the tubular housing and the two legs of the frame, wherein the fixing device comprises a pair of rods provided with a bracket arranged on the top of each rod for connecting the rods to the first end unit via bolts.

* * * * *